(12) United States Patent
Zhou et al.

(10) Patent No.: US 6,462,243 B1
(45) Date of Patent: Oct. 8, 2002

(54) INTEGRATED PROCESS FOR SYNTHESIZING ALCOHOLS AND ETHERS FROM ALKANES

(75) Inventors: Xiao Ping Zhou, Goleta, CA (US); Ivan Marc Lorkovic, Santa Barbara, CA (US); Galen D. Stucky, Goleta, CA (US); Peter C. Ford, Santa Barbara, CA (US); Jeffrey H. Sherman, The Woodlands, TX (US); Philip Grosso, Auburn, CA (US)

(73) Assignees: GRT, Inc., The Woodland, TX (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 09/951,570

(22) Filed: Sep. 11, 2001

Related U.S. Application Data

(63) Continuation-in-part of application No. 09/886,078, filed on Jun. 20, 2001.

(51) Int. Cl.[7] .................. C07C 27/00; C07C 41/00; C07O 27/10
(52) U.S. Cl. ............... 568/893; 568/671; 568/891; 568/910
(58) Field of Search .................. 568/671, 891, 568/893, 910

(56) References Cited

U.S. PATENT DOCUMENTS

| | | | |
|---|---|---|---|
| 3,172,915 A | 3/1965 | Borkowski et al. | 260/614 |
| 3,310,380 A | 3/1967 | Lester | 23/216 |
| 5,243,098 A | 9/1993 | Miller et al. | 568/893 |
| 5,334,777 A | 8/1994 | Miller et al. | 568/859 |
| 5,998,679 A | 12/1999 | Miller | 568/859 |

FOREIGN PATENT DOCUMENTS

| WO | PCT/IE99/05576 | 7/1999 |
|---|---|---|

OTHER PUBLICATIONS

Selective Monohalogenation of Methane over Supported Acid or Platinum Metal Catalysts and Hydrolysis of Methyl Halides over y–Alumina–Supported Metal Oxide/Hydroxide Catalysts. A Feasible Path for the Oxidative Conversion of Methane into Methyl Alcohol/Dimethyl Ether: George B. Olah, et al.; Contribution from the Donald P. and Katherine B. Loker Hydrocarbon Research Institute and Department of Chemistry, University of Southern California, Los Angeles, CA, received Apr. 22, 1985.

*Primary Examiner*—Samuel Barts
*Assistant Examiner*—Elvis O. Price
(74) *Attorney, Agent, or Firm*—Michael A. O'Neil

(57) ABSTRACT

Alcohols and/or ethers are synthesized from alkanes by mixing an alkane and bromine in a reactor to form alkyl bromide and hydrogen bromide. The alkyl bromide is directed into contact with metal oxide to form alcohol and/or ether and a metal bromide. The metal bromide is oxidized to metal oxide and bromine, both of which are recycled.

41 Claims, 4 Drawing Sheets

ABSTRACT

INTEGRATED PROCESS FOR SYNTHESIZING ALCOHOLS AND ETHERS FROM ALKANES

CROSS-REFERENCE TO RELATED APPLICATIONS

This is a continuation-in-part application under 37 C.F.R. §1.53 of Application Ser. No. 09/886,078 filed Jun. 20, 2001, currently pending.

TECHNICAL FIELD

This invention relates generally to the synthesis of alcohols and ethers from alkanes, and more particularly to a method of and apparatus for manufacturing methanol and dimethyl ether from methane.

BACKGROUND OF THE INVENTION

Methane has previously been converted to methanol by the halogenation of methane followed by hydrolysis of the methyl halide to form methanol. For. example, gaseous chlorine has been used to chlorinate methane to form chlorinated methane, principally methyl chloride, together with other chlorides, i.e., dichloromethane, trichloromethane and carbon tetrachloride. Alternatively, methane has been subjected to oxychlorination with oxygen and hydrochloric acid to form the foregoing compounds. The chlorinated methanes produced are hydrolyzed in the vapor phase to produce methanol, formaldehyde, formic acid and by-products, including carbon dioxide and hydrochloric acid, depending on the chlorination selectivity. Hydrochloric acid is produced or used in the halogenation of methane by either method and must be recovered, dehydrated by azeotropic distillation and recycled. Corrosion and other problems involved with the handling of chlorine and hydrochloric acid are substantial.

U.S. Pat. No. 3,172,915 granted to Borkowski, et al. is directed to a process for converting methane to methanol. Borkowski discloses the chlorination of methane using ferric chloride at high temperatures to produce chloromethanes and hydrogen chloride. The process requires temperatures in the range of 220–8002° C., more preferably 250–450° C., and long residence times, e.g., more than one hour. Further, the process is hindered by the production of a mixture of chlorination products, e.g., chloromethane, dichloromethane, trichloromethane and carbon tetrachloride, which must be separated before hydrolysis to methanol. Other disadvantages result from the energy required to dry the ferric chloride and from the corrosion and handling problems inherent with hydrochloric acid.

U.S. Pat. No. 5,243,098 granted to Miller discloses another method for converting methane to methanol. In the Miller process the reaction of methane with cupric chloride produces chloromethane and hydrochloric acid. These intermediates are then reacted with steam and a catalyst containing magnesium oxide to produce methanol and magnesium chloride. Magnesium oxide is regenerated by treatment of the magnesium chloride by-product with air or oxygen. Cupric chloride is regenerated by treatment of the cuprous chloride by-product with air and hydrochloric acid. While these reactions proceed at favorable rates, attrition of the solid reactants, i.e., cupric and magnesium oxide, is significant. Special filters and processes are required to recover and regenerate the reactants in the required particle size. Miller also suggests cupric bromide and magnesium zeolite as alternative reactants. Because of the attrition of the reactants, difficulties associated with the handling of solids, and the special filters and processes required to regenerate the reactants, the Miller process has proven unsatisfactory. U.S. Pat. No. 5,334,777, also granted to Miller, discloses a nearly identical process for converting ethane to ethylene glycol.

U.S. Pat. No. 5,998,679 granted to Jorge Miller, discloses a process for converting alkanes and alkenes to the corresponding lower alkanols and diols. In the method of the invention, a gaseous halogen (bromine) is produced by decomposing a metal halide in a liquid having a melting point below and a boiling point above the decomposition temperature of the metal halide. The preferred liquid is molten hydrated ferric chloride maintained at a temperature between about 37–280° C. The lower alkane or alkene is halogenated in a gas phase reaction with the halogen. The resulting alkyl halide or alkyl dihalide is contacted with a metal hydroxide, preferably an aqueous solution of ferric hydroxide, to regenerate the metal halide and produce the corresponding lower alkanol or diol. Problems with this process include low monohalogenation selectivity, and corrosiveness of the hydrated ferric halides, which may present a containment problem if the process is run at 280° C., where high pressures of steam are required to maintain ferric halide hydration. Finally, the process produces a great deal of water and HCl or HBr, all of which are difficult to separate on a large scale from the desired product methanol.

Published international patent application WO 00/07718, naming Giuseppe Bellussi, Carlo Perego, and Laura Zanibelli as inventors, discloses a method for directly converting methane and oxygen to methanol over a metal halide/metal oxide catalyst. This is not a catalyst in the true sense of the word, however, because the reaction involves transfer of halide from a metal halide via reaction with methane to a different metal oxide producing the metal halide and methanol downstream. Eventually the halide is leached and the catalyst loses activity.

Olah et al. (George A. Olah, et al. J. Am. Chem. Soc. 1985, 107, 7097–7105) discloses a method for converting methane to methanol via methyl halides ($CH_3Br$ and $CH_3Cl$), which are then hydrolyzed to prepare methanol. In the process, $CH_3Br$ and $CH_3Cl$ are hydrolyzed over catalysts with excess steam generating a methanol, water, and HCl or HBr mixture. The separation of methanol (about 2% by mole) from HCl or HBr and water on an industry scale (2000 tons per day) requires an enormous amount of energy and generates a great deal of aqueous HCl or HBr waste. Aqueous HCl and HBr are very corrosive as well.

SUMMARY OF THE INVENTION

The present invention comprises a process wherein bromine or a bromine containing compound is used as an intermediate to convert alkanes to alcohols, ethers, or olefins by reaction with oxygen or air. While the process can be used to convert a variety of alkanes, including methane, ethane, propane, butane, isobutane, pentanes, hexanes, cyclohexane, etc. to their respective alcohols, ethers, or olefins, the conversion of methane to methanol and dimethyl ether is illustrative.

Methane reacts with bromine over a catalyst to form $CH_3Br$ and HBr. $CH_3Br$ and HBr react with a metal oxide to form a variable mixture of dimethyl ether (DME), water and methanol, and the metal bromide. The metal oxide and molecular bromine are regenerated by reaction of the metal bromide with air and/or oxygen. The regenerated bromine is recycled to react with methane while the regenerated metal oxide is used to convert more methyl bromide to methanol and DME, completing the reaction cycle.

The process can be easily carried out in a riser reactor. Compared to the current industrial two step process, in which methane and steam are first converted to CO and $H_2$ at 800° C. followed by conversion to methanol over a Zn—Cu—Al—O catalyst at approximately 70–150 atmospheres, the process of the present invention operates at roughly atmospheric pressure and relatively low temperatures, thereby providing a safe and efficient process for methanol production.

The present invention operates with solid/gas mixtures at atmospheric pressure. In the process, the hydrogen halide is gaseous, and therefore not as corrosive as when aqueous at high temperatures. The reaction of $Br_2$ with an alkane can reach more than 90% selectivity and high conversion to alkane-monobromide. The main side products, alkane dibromides such as $CH_2Br_2$ can be converted back to the monobromides by reaction with an alkane over another catalyst. Very few by-products are produced.

In the process most of the Br atoms are trapped in the solid state, making the system less corrosive.

Another advantage is that DME and alcohol ($CH_3OH$) are not produced as a mixture with excess water. By controlling reaction conditions, almost pure DME and/or methanol is obtained directly so that it is not necessary to separate $CH_3OH$ from water. Finally, in the present process, methane and oxygen do not come into direct contact, resulting in improved safety.

BRIEF DESCRIPTION OF THE DRAWINGS

A more complete understanding of the present invention may be had by reference to the following Detailed Description when taken in connection with the accompanying Drawings, wherein.

DETAILED DESCRIPTION

Alkanes (methane, ethane, propane, butane, isobutane, pentanes, hexanes, cyclohexane, etc.) react with molecular bromine over a catalyst composed of all possible metal compounds and mixtures thereof to form alkylbromides. For $CH_4$ (although the process may be applied to higher alkanes as well), the process of the present invention can convert more than 50% $CH_4$ to $CH_3Br$ and HBr, with selectivity higher than 90%. Most of the by-product is $CH_2Br_2$ (with trace amounts of $CHBr_3$, and $CBr_4$) (+2 HBr), which can be catalytically reconverted to $CH_3Br$ by reacting $CH_2Br_2$ with $CH_4$.

Figure 1:
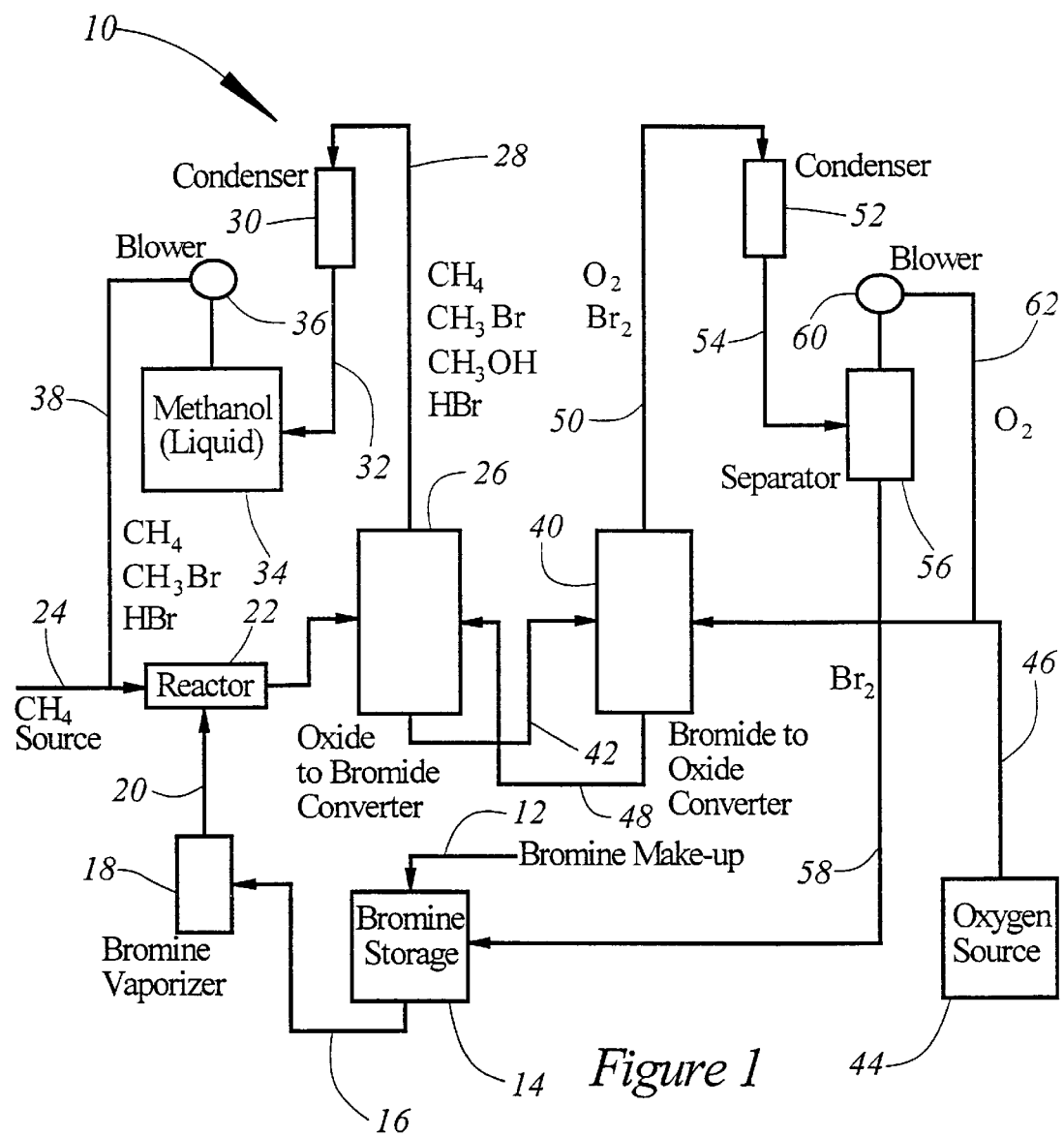
FIG. 1 is a schematic illustration of a method of and apparatus for synthesizing alcohols and/or ethers from alkanes comprising a first embodiment of the invention.

Referring to the Drawings, and particularly to FIG. 1, a method and apparatus 10 for synthesizing alcohols and ethers from alkanes using bromine comprising a first embodiment of the invention is schematically illustrated. In the operation of the method and apparatus 10, bromine is received from a suitable source through a line 12 and is directed to a bromine storage container 14. For example, bromine is easily manufactured from bromide, which is readily available from sea water.

As is well known, bromine is a liquid at room temperature. Liquid bromine from the storage container 14 is directed through a line 16 to a bromine vaporizer 18 wherein the bromine is converted from the liquid phase to the gas phase. From the vaporizer 18 the gaseous bromine is directed through a line 20 to a reactor 22.

Methane from a suitable source is directed to the reactor 22, which contains a bromination catalyst, through a line 24. Within the reactor 22 the methane and the gaseous bromine are mixed together and the temperature of the mixture is raised to between about 20° C. and about 600° C., thereby converting the methane and the bromine to methyl bromide ($CH_3Br$) and hydrogen bromide (HBr).

From the reactor 22, the $CH_3Br$, the HBr, any unreacted methane and by products $CH_2Br_2$, $CHBr_3$, and $CBr_4$ are directed to a condenser 34. The by products $CH_2Br_2$, $CHBr_{31}$ and $CBr_4$ now in the liquid states are sent to a converter 28 with methane from the line 24. In converter 28, methane reacts with the by products $CH_2Br_2$, $CHBr_3$, and $CBr_4$ to form $CH_3Br$. The newly formed $CH_3Br$ and any unreacted $CH_2Br_{21}$, $CHBr_3$, $CBr_4$ and/or methane are sent to the condenser 34. From the condenser 34, the gas phase methane, HBr, and $CH_3Br$ are sent to a converter 52. In the converter 52 HBr and $CH_3Br$ react with metal oxide to form $CH_3OCH_{31}$, $CH_3OH$, and $H_2O$, which are sent to a separator 44 along with unreacted methane and $CH_3Br$. In the separator, methanol and dimethyl ether are separated as products. $CH_3Br$ is sent back to the converter 52. Methane is sent back to the bromination reactor 22. In the converter 52, the original metal oxide has been converted to metal bromide after reaction. The metal bromide is sent to a converter 58 to react with oxygen (from source 74) to regenerate bromine and metal oxide. The regenerated metal oxide is sent back to the converter 52, while the bromine and unreacted oxygen are sent to a condenser 62, then to a separator 68. The liquid bromine is sent to the storage container 14, while oxygen is sent to the converter 58.

Figure 2:
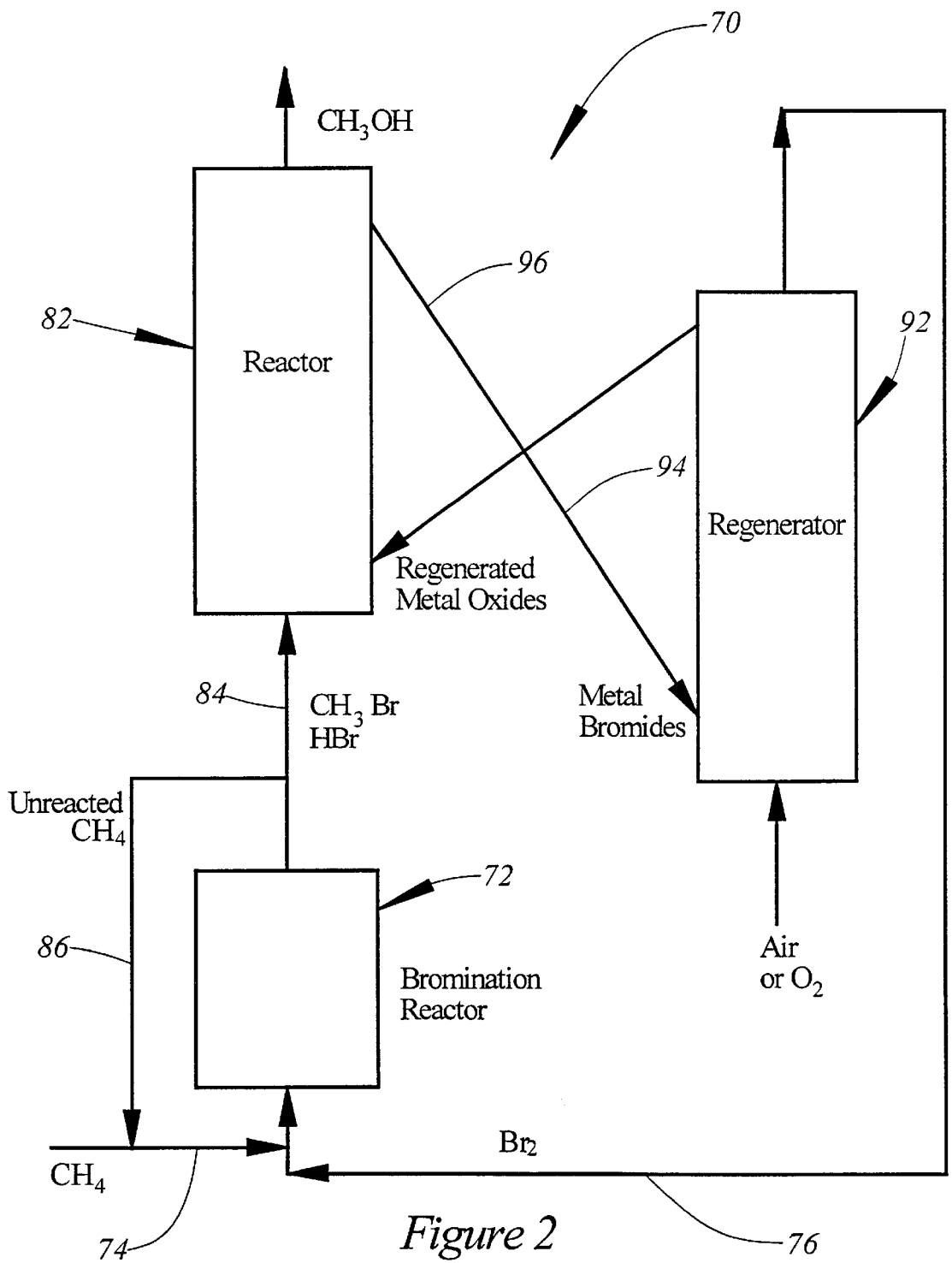
FIG. 2 is a schematic illustration of a method of and apparatus for synthesizing alcohols and/or ethers from alkanes comprising a second embodiment of the invention.

Referring to FIG. 2, there is shown a method of and apparatus 100 for synthesizing alcohols and ethers from alkanes comprising a second embodiment of the invention. Methane and bromine are directed to a heated vaporizer 102 where they are heated to form a gas mixture. The gas mixture is passed into a bromination reactor 104, containing a bromination catalyst, if desired. After the reaction, the mixture is directed to a condenser 106. The liquid phase contains by products $CH_2Br_2$, $CHBr_3$, and $CBr_4$, while the gas phase contains bromomethane, HBr, and unreacted methane.

The liquid by products $CH_2Br_2$, $CHBr_3$, and $CBr_4$ are sent to a converter 108 where they react with methane to form bromomethane. After reaction the mixture is sent to the condenser 106, where any remaining byproducts can once again be cycled to the converter 108.

The gas phase mixture from condenser 106 is passed through a converter 110, where HBr reacts with metal oxide to form metal bromide and water. The metal bromide is sent to a regenerator 120 to regenerate metal oxide. From the converter 110, the water, bromomethane, and methane are separated. Methane is recycled to the converter 108 and the vaporizer 102. Bromomethane is sent to a reactor 114. Water is sent to a reactor 118.

In the reactor 114, bromomethane reacts with metal oxide to generate dimethyl ether (DME) and metal bromide. Metal bromide is sent to the regenerator 120.

The mixture of bromomethane and DME from the reactor 114 is sent to a separator 116. Bromomethane from the separator 116 is recycled to the reactor 114, while DME is obtained as a product or directed to the reactor 118.

In the reactor 118, DME reacts with water, e.g., from the separator 112, over a suitable catalyst to form methanol.

In the regenerator 120, metal bromide from the converter 110 and the reactor 114 reacts with air or oxygen to regenerate metal oxide and bromine. After regeneration, metal oxide is sent to the converter 110 and the reactor 114, while bromine is sent to the vaporizer 102. If air is used as the source of oxygen, nitrogen can be continuously purged from the system through a separator 122.

Figure 3:
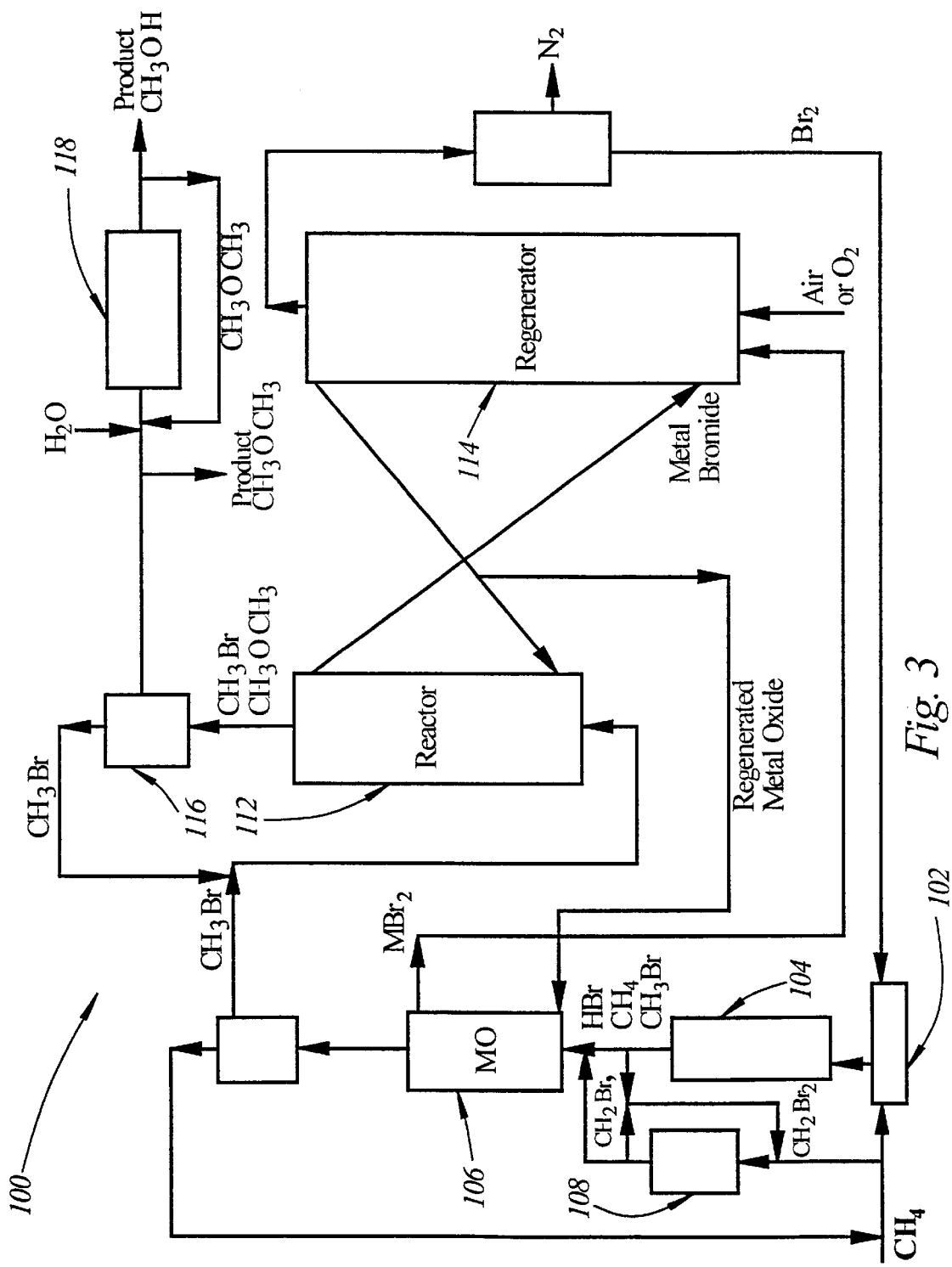
FIG. 3 is a schematic illustration of a method of and apparatus for synthesizing ethers and/or alcohols from alkanes comprising a third embodiment of the invention.
Figure 4:
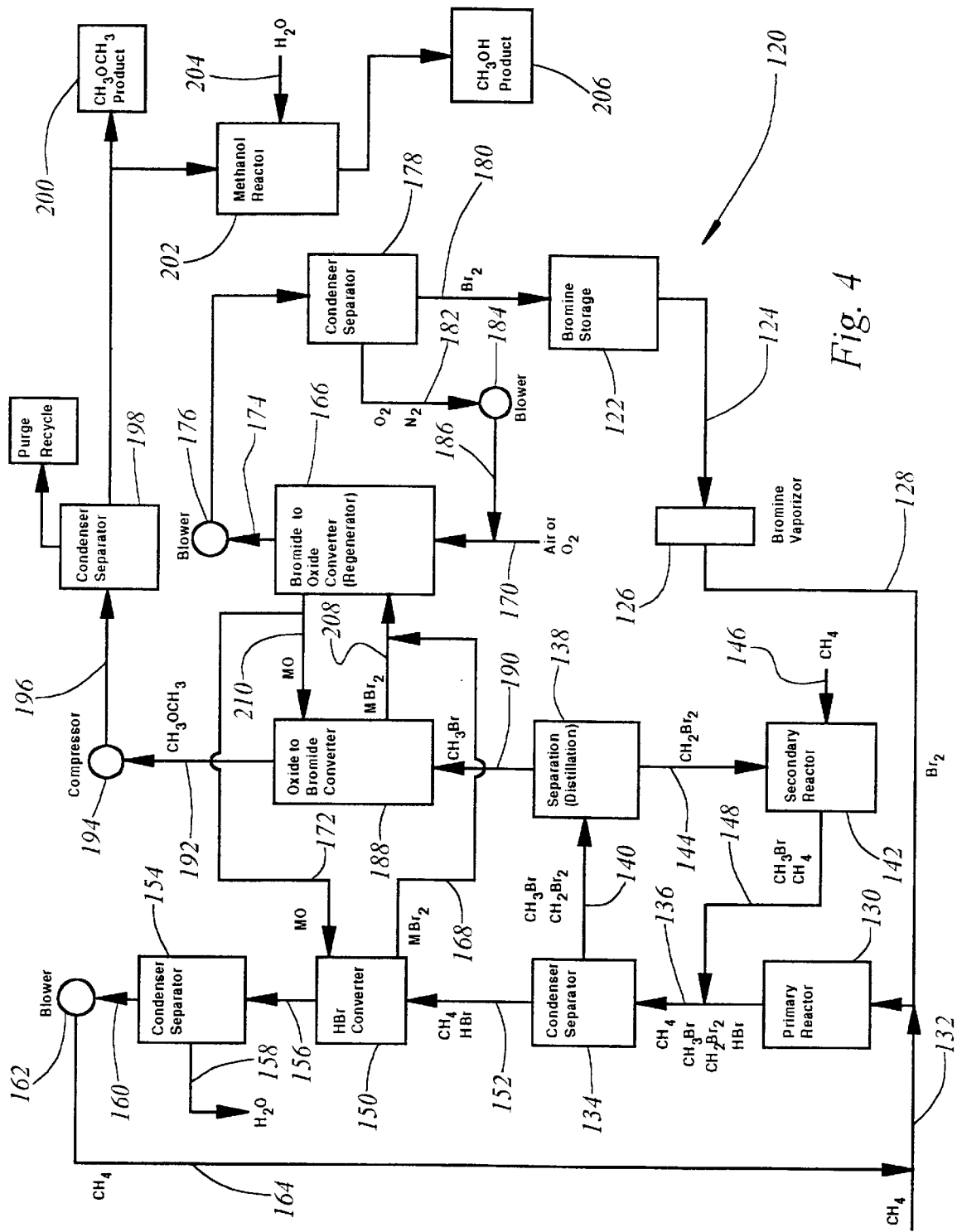
FIG. 4 is a schematic illustration of a method of and apparatus for synthesizing ethers and/or alcohols from alkanes comprising a fourth embodiment of the invention.

A method and apparatus 121 for converting methane to dimethyl ether and/or methanol comprising a third embodiment of the invention is illustrated in FIG. 3. Liquid bromine is stored in a bromine storage container 123 and is directed therefrom through a line 124 through a bromine vaporizer 126. From the bromine vaporizer 126 the bromine vapor passes through a line 128 to a primary reactor 130 which also receives methane from a suitable source through a line 132.

Within the primary reactor 130, the bromine and methane react over a solid catalyst, if desired, to form $CH_3Br$, $CH_2Br_2$, $CHBr_3$, $CBr_4$ and HBr. The reaction products together with any unreacted methane are directed to a condenser separator 134 through a line 136. The condenser separator 134 directs $CH_3Br$, $CH_2Br_2$, $CHBr_3$; and $CBr_4$ to a separation (distillation) apparatus 138 through a line 140. The separation (distillation) apparatus 138 directs $CH_2Br_2$, $CHBr_3$, and $CBr_4$ to a secondary reactor 142 through a line 144. The secondary reactor 142 also receives methane from a suitable source through a line 146.

The secondary reactor 142 converts the $CH_2Br_2$, $CHBr_3$, and $CBr_4$ received through the line 144 to $CH_3Br$. $CH_3Br$ and excess methane are directed from the secondary reactor 142 to the line 136 through a line 148.

The condenser separator 134 also directs $CH_4$ and HBr to an HBr converter 150 through a line 152. The HBr converter 150 is filled with a metal oxide. Within the HBr converter 150 the metal oxide and the HBr react to form metal bromide and water. The water and the unreacted methane are directed from the HBr converter 150 to a condenser separator 154 through a line 156. The water is recovered from the condenser separator 154 through an outlet 158, while the unreacted methane is directed through a line 160 to a blower 162 and from the blower 162 through a line 164 to the line 132.

Metal bromide formed during operation of the HBr converter 150 is directed to a bromide to oxide converter (regenerator) 166 through a line 168. The bromide to oxide converter 166 receives air or oxygen through a line 170 and functions to convert the metal bromide back to metal oxide. The metal oxide is returned to the HBr converter 150 through a line 172.

Operation of the bromide to oxide converter 166 also produces bromine. Bromine and excess air or oxygen are directed through a line 174 to a blower 176, and from the blower 176 to a condenser separator 178. Operation of the condenser separator 178 produces liquid bromine which is directed to the bromine storage container 123 through a line 180. Excess air and/or oxygen is recovered from the condenser separator 178 through an outlet 182 and is directed therefrom through a blower 184 and a line 186 to the line 170.

The separation (distillation) apparatus 138 directs $CH_3Br$ to an oxide to bromide converter 188 through a line 190. The oxide to bromide converter 188 is filled with a metal oxide, which may be the same metal oxide that is utilized in the operation of the HBr converter 150. Operation of the oxide to bromide converter 188 produces dimethyl ether, which together with unreacted bromomethane is directed through a line 192, a compressor 194, and a line 196 to a condenser separator 198. From the condenser separator 198 dimethyl ether may be recovered as a final product at an outlet 200. The bromomethane is sent back to the converter 188. Alternatively, the dimethyl ether may be directed to a methanol reactor 202, which receives water through an inlet 204. The dimethyl ether and the water react in the methyl reactor 202 to form methanol, which is recovered at an outlet 206.

Operation of the oxide to bromide converter 188 converts the metal oxide contained therein to metal bromide, which is directed to the bromide to oxide converter 166 through a line 208. Operation of the bromide to oxide converter 166 converts the metal bromide to the original metal oxide, which is returned to the oxide to bromide converter 188 through a line 210.

EXAMPLES

Reaction 1

Catalyst Preparation $Nb_2O_5$ (0.8000 g) was mixed with 0.500 ml 96(w)% $H_2SO_4$, then the mixture was heated at 110° C. for 4 hours. The temperature increased to 500° C. within 6 hours, and kept at 500° C. for 4 hours. Catalyst C1 was obtained.

Testing

Reaction conditions:

The catalyst was tested at a methane flow of 1.5 ml/minute and $Br_2$ flow of 0.07 ml/hour. The reaction temperature was 400° C. The reaction was carried out in a microreactor system. After 6 hours on line reaction, the reaction effluent was analyzed by a GC/MS. A methane conversion of 24% (mol) with 95% $CH_3Br$ was obtained. Summarizing the overall process in Reaction 1:

$$CH_4+Br_2>HBr+CH_3Br+CH_2Br_2+CHBr_3 \text{cat} \qquad (1)$$

Reaction 2

Metal Oxide Preparation

Zr Solution Preparation $Zr(OCH_2CH_2CH_3)_4$ (70(w)% in isopropanol, 112.6 ml) was dissolved into acetic acid (275 ml) under stirring. After stirring for 10 minutes, the solution was diluted by water to make a total volume of 500 ml. A solution with a Zr concentration of 0.5M was obtained.

Preparation of M1

$Cu(NO_3)_2$ (0.5M, 7.200 ml) solution was added into $BaBr_2$ (0.5M, 0.800 ml). A clear solution was obtained. To this solution, Zr solution (0.5M) as prepared above was added under stirring. After stirring a few seconds, a gel was obtained. The gel was dried at 110° C. for 4 hours, then heated to 500° C. within 6 hours, and kept at 500° C. for 4 hours. M1 was obtained. The metal oxide mixture was tested at a $CH_3Br$ flow of 1.0 ml/minute at 230° C. In the first half hour, the average $CH_3Br$ conversion is 65%, and the average dimethyl ether selectivity is 90.5%.

Catalyst Preparation $ZrO_2$ (2.0000 g) was mixed with $H_2SO_4$ (3.000 ml, 96(w)%), then the mixture was heated at 110° C. for 4 hours. The temperature increased to 500° C. within 6 hours, and kept at 500° C. for 4 hours. Catalyst C2 was obtained.

Preparation of M2

$Cu(NO_3)_2$ (0.5M, 40.000 ml) solution was added into Zr solution (0.5M, 30.000 ml as prepared above). After stirring a few seconds, a gel was obtained. The gel was dried at 110° C. for 4 hours, then heated to 500° C. within 6 hours, and calcined at 500° C. for 4 hours. M2 was obtained.

Testing

The catalyst C2 (2.0000 g) was loaded in the first reactor (R1). A trap was loaded 2.0000 g M2 in the oxide form. A second reactor (R2) was also loaded with M2 in the oxide form(0.8500 g).

Reactants methane and bromine were fed into the first reactor (methane flow of 1.5 ml/minute, $Br_2$ flow of 0.07 ml/hour). The reaction temperature was 390° C. After the reaction in R1 (stabilized by online reaction for more than 8 hours), the products generated in R1 were passed through the trap and HBr was removed. Following removal of HBr, a mixture of methane and $CH_3Br$ (containing 20% mol of $CH_3Br$) was obtained. This gas mixture was directly fed into R2 at 220° C. In the first one hour, an average $CH_3Br$ conversion of 91% with an average dimethyl ether selectivity of 75% was obtained.

Summarizing the overall process in Reaction 2:

$$CH_3Br+HBr+CuO>CH_3OH+CuBr_2 \qquad (2)$$

Possible variations of Reaction 2:

$$2HBr+CuO>H_2O+CuBr_2 \text{ (reaction occurring in the trap)} \qquad (2a)$$

$$2CH_3Br+CuO>CH_3OCH_3+CuBr_2 \qquad (2b)$$

Reaction 3

The solid $CuBr_2/ZrO_2$ is transferred from Reactor 2 to Reactor 3 and treated with $O_2$ at 300° C. to yield $Br_2$ and $CuO/ZrO_2$ in 100% yield and conversion. This reaction may be run at space velocity 100 $h^{-1}$. Summarizing the overall process in Reaction 3:

$$CuBr_2/ZrO_2+\tfrac{1}{2}O_2>Br_2+CuO/ZrO_2 \qquad (3)$$

Overall:

$$CH_4+\tfrac{1}{2}O_2>CH_3OH \qquad (A)$$

Possible variation:

$$CH_4+\tfrac{1}{2}O_2>\tfrac{1}{2}CH_3OCH_3+\tfrac{1}{2}H_2O \qquad (B)$$

It will therefore be understood that the method and apparatus of the present invention operates on a continuous or batch basis to convert alkanes to alcohols and ethers. The method and apparatus of the present invention operates at relatively low temperatures and at low pressures and is therefore economical for manufacture and use. The bromine, which is utilized in the method and apparatus of the present invention, is continuously recycled. The metal oxide catalyst, which is utilized in the process is continuously refreshed.

Although preferred embodiments of the invention have been illustrated in the accompanying drawings and described in the foregoing detailed description, it will be understood that the invention is not limited to the embodiments disclosed but is capable of numerous rearrangements, modifications, and substitutions of parts and elements without departing from the spirit of the invention.

What is claimed is:

1. A method for synthesizing alcohols and/or ethers from alkanes comprising:

providing a quantity of an alkane selected from the group including methane, ethane, propane, butane, and isobutane;

providing a quantity of bromine;

mixing the alkane and the bromine and thereby forming an alkyl bromide and hydrogen bromide;

directing the hydrogen bromide into engagement with a metal oxide and thereby forming a metal bromide and water;

converting the metal bromide from the hydrogen bromide metal oxide reaction to form the original metal oxide;

separately directing the alkyl bromide into engagement with a metal oxide and thereby forming alcohol and/or ether and a metal bromide;

converting the metal bromide from the alkyl bromide metal oxide reaction to form the original metal oxide and bromine;

recycling the metal oxide; and recycling the bromine.

2. The method according to claim 1 wherein the step of mixing the alkane and the bromine is carried out at an alkane to bromine molar ratio from 1:10 to 100:1.

3. The method according to claim 1 wherein the step of mixing the alkane and the bromine is carried out at a temperature of between about 20° C. and about 600° C.

4. The method according to claim 1 wherein the step of mixing the alkane and the bromine is carried out at a pressure between 0.1 to 200 atm.

5. The method according to claim 1 wherein the step of reacting the alkane with the bromine to form the alkyl bromide and hydrogen bromide with metal oxide and the step of contacting the alkyl bromide with metal oxides are carried out continuously.

6. The method according to claim 1 wherein the step of reacting the alkane with the bromine to form the alkyl bromide and hydrogen bromide and the step of contacting the alkyl bromide with metal oxide are carried out in a batch reaction.

7. The method according to claim 1 wherein the step of converting the metal bromide to form the original metal oxide and bromine, the step of recycling the metal oxide, and the step of recycling the bromine are carried out continuously.

8. The method according to claim 1 wherein the istep of converting the metal bromide to form the original metal oxide and bromine, the step of recycling the metal oxide, and the step of recycling the bromine are carried out in a batch reaction.

9. The method according to claim 1 wherein the alkyl bromide and the hydrogen bromide are separately directed into engagement with the same metal oxide.

10. The method according to claim 1 wherein the alkyl bromide and the hydrogen bromide are separately directed into engagement with different metal oxides.

11. A method for converting methane to methanol comprising:
providing a quantity of methane;
providing a quantity of bromine;
reacting the methane with the bromine and thereby forming methyl bromide and hydrogen bromide;
directing the methyl bromide into engagement with a metal oxide and thereby forming methanol and a metal bromide;
converting the metal bromide resulting from the methyl bromide metal oxide reaction to form the original metal oxide and bromine;
separately directing the hydrogen bromide into engagement with a metal oxide to form water and a metal bromide;
converting the metal bromide resulting from the hydrogen bromide metal oxide reaction to form the original metal oxide and bromine;
recycling the metal oxides; and
recycling the bromine.

12. The method according to claim 11 wherein the step of mixing the methane and the bromine is carried out at a methane to bromine ratio from about 1:10 to about 100:1 (by mole).

13. The method according to claim 11 wherein the step of mixing the methane and the bromine is carried out at a methane to bromine ratio from about 1:1 to about 10:1 (by mole).

14. The process according to claim 11 wherein the step of mixing the methane and the bromine is carried out at a methane to bromine ratio from about 1:1 to about 5:1 (by mole).

15. The method according to claim 11 wherein the step of mixing the methane and the bromine is carried out at a temperature of between about 20° C. and about 600° C.

16. The method according to claim 11 wherein the step of mixing the methane and the bromine is carried out at a pressure between 0.1 and 200 atm.

17. The process according to claim 11 wherein the step of mixing the methane and the bromine to form the methyl bromide and hydrogen bromide and the step of contacting the methyl bromide with a metal oxide are carried out continuously.

18. The process according to claim 11 wherein the step of mixing the methane and the bromine to form the methyl bromide and hydrogen bromide and the step of contacting the methyl bromide with a metal oxide are carried out in a batch reaction.

19. The method according to claim 11 wherein the step of converting the metal bromide to form the original metal oxide catalyst and bromine, the step of recycling the metal oxide, and the step of recycling the bromine are carried out continuously.

20. The method according to claim 11 wherein the step of converting the metal bromide to form the original metal oxide catalyst and bromine, the step of recycling the metal oxide, and the step of recycling the bromine are carried out in a batch reaction.

21. A method for synthesizing ethers from alkanes comprising:
providing a quantity of an alkane;
providing a quantity of bromine;
mixing the alkane and the bromine and thereby forming an alkyl bromide and hydrogen bromide;
directing the alkyl bromide into engagement with a metal oxide and thereby forming an ether and a metal bromide;
converting the metal bromide from the alkyl bromide metal oxide reaction to form metal oxide and bromine;
separately directing the hydrogen bromide into engagement with a metal oxide to form water and a metal bromide;
converting the metal bromide from the hydrogen bromide metal oxide reaction to form metal oxide and bromine;
recycling the metal oxide; and
recycling the bromine.

22. The method according to claim 21 wherein the step of mixing the alkane and the bromine is carried out at a alkane to bromine mol ratio between about 1:10 to about 100:1.

23. The method according to claim 21 wherein the step of mixing the alkane and the bromine is carried out at a alkane to bromine mol ratio between about 1:5 to about 50:1.

24. The method according to claim 21 wherein the step of mixing the alkane and the bromine is carried out at a alkane to bromine mol ratio between about 1:2 to about 10:1.

25. The method according to claim 21 wherein the step of mixing the alkane and the bromine is carried out at a temperature of between about 20° C. and about 600° C.

26. The method according to claim 21 wherein the step of mixing the alkane and the bromine is carried out at a pressure between 0.1 and 200 atm.

27. The process according to claim 21 wherein the step of mixing the alkane and the bromine to form the alkyl bromide and hydrogen bromide and the step of contacting the alkyl bromide with a metal oxide are carried out continuously.

28. The process according to claim 21 wherein the step of mixing the alkane and the bromine to form the alkyl bromide and hydrogen bromide and the step of contacting the alkyl bromide with a metal oxide are carried out in a batch reaction.

29. The method according to claim 21 wherein the step of converting the metal bromide to form the original metal oxide catalyst and bromine, the step of recycling the metal oxide catalyst, and the step of recycling the bromine are carried out continuously.

30. The method according to claim 21 wherein the step of converting the metal bromide to form the original metal oxide catalyst and bromine, the step of recycling the metal oxide, and the step of recycling the bromine are carried out in batch reactions.

31. A method for converting methane to dimethyl ether comprising:

providing a quantity of methane;

providing a quantity of bromine;

mixing the methane and the bromine and thereby forming methyl bromide and hydrogen bromide;

trapping the hydrogen bromide by reacting it with a metal oxide;

directing the methyl bromide into engagement with a metal oxide and thereby forming dimethyl ether and a metal bromide;

converting the metal bromide resulting from the methyl bromide metal oxide reaction to form the original metal oxide and bromine;

recycling the metal oxide; and recycling the bromine.

32. The method according to claim 31 wherein the step of mixing the methane and the bromine is carried out at a methane to bromine mol ratio between about 1:10 to about 100:1.

33. The method according to claim 31 wherein the step of mixing the methane and the bromine is carried out at a methane to bromine mol ratio between about 1:5 to about 50:1.

34. The method according to claim 31 wherein the step of mixing the methane and the bromine is carried out at a methane to bromine mol ratio between about 1:2 to about 10:1.

35. The method according to claim 31 wherein the step of mixing the methane and the bromine is carried out at a temperature of between about 20° C. and 600° C.

36. The method according to claim 31 wherein the step of mixing the methane and the bromine is carried out at a pressure of between 0.1 and 200 atm.

37. The process according to claim 31 wherein the step of mixing the methane and the bromine to form the methyl bromide and hydrogen bromide, the step of trapping the hydrogen bromide, and the step of contacting the methyl bromide with metal oxide are carried out continuously.

38. The method according to claim 31 wherein the step of converting the metal bromide to form metal oxide and bromine, the step of recycling metal oxide, and the step of recycling the bromine are carried out continuously.

39. The method according to claim 31 wherein the step of trapping the hydrogen bromide by reacting it with metal oxide produces water and metal bromide.

40. The method according to claim 31 wherein the metal oxide which reacts with the methyl bromide and the metal oxide which reacts with the hydrogen bromide are the same metal oxide.

41. The method according to claim 31 wherein the metal oxide which reacts with the methyl bromide and the metal oxides which reacts with the hydrogen bromide are different metal oxides.

* * * * *